United States Patent [19]

Widder

[11] 3,987,161

[45] Oct. 19, 1976

[54] COMPOSITION AND METHOD FOR CONDITIONING HAIR WITH HAIR ANTISERUM

[75] Inventor: James Stone Widder, Springfield Township, Hamilton County, Ohio

[73] Assignee: The Procter & Gamble Company, Cincinnati, Ohio

[22] Filed: June 19, 1974

[21] Appl. No.: 480,910

[52] U.S. Cl. .................................. 424/70; 424/12; 424/85; 424/88; 424/177
[51] Int. Cl.² ................... A61K 7/06; A61K 37/00; A61K 39/00
[58] Field of Search .............. 424/8, 12, 70, 85, 88, 424/177

[56] References Cited
FOREIGN PATENTS OR APPLICATIONS

| 1,802,386 | 11/1969 | Germany | 424/177 |
| A22,643 | 1907 | United Kingdom | 424/70 |

OTHER PUBLICATIONS

Moschetto, Chem. Abs., vol. 68, 1968, p. 2595, Ab. No. 26968a.
Kemp, Chem. Abs., vol. 74, 1971, p. 176, Ab. No. 11482n.
Walzer, Arch. Derm., vol. 93, June, 1966, pp. 758–762.
Matoltsy, J. Invst. Dermatol., vol. 41, 1963, pp. 255–257.
Ishizaka, J. Immunol., vol. 83, 1959, pp. 105–115.
Fisher, J. Inst. Dermatol., vol. 47, 1966, pp. 336–350.
Aerosol Age, Dec. 1969, pp. 30–32, 34, 36, 38, 39.
DeNavarre, Chem. & Mfg. Cosmetics, D. Van Nostrand & Co., N.Y., 2nd Ed., vol. II, 1962, pp. 239–245.
Moschetto, CR Acd. Sc, Paris, vol. 265(D), 2 Oct. 1967, pp. 1004–1006.
Kemp, J. Cell. Sci, vol. 7, 1970, pp. 273–283.

*Primary Examiner*—James O. Thomas, Jr.
*Assistant Examiner*—A. P. Fagelson
*Attorney, Agent, or Firm*—Ronald L. Hemingway; Jerry J. Yetter; George W. Allen

[57] ABSTRACT

Conditioning hair by applying thereto an antiserum which is prepared by injecting a suspension of hair particles into an animal, withdrawing blood from the animal, and isolating the antiserum from the blood by conventional means. Also disclosed are shampoo compositions containing said antiserum.

6 Claims, No Drawings

COMPOSITION AND METHOD FOR CONDITIONING HAIR WITH HAIR ANTISERUM

BACKGROUND OF THE INVENTION

The use of proteinaceous materials as hair conditioning additives in hair treating products such as shampoos is known in the art. However, the proteinaceous materials which have been used heretofore do not have a high degree of substantivity to the hair, and therefore, they are not particularly effective in conditioning the hair.

It is an object of the present invention to provide proteinaceous materials which are highly substantive to the hair and which impart an improved "body", "set" retention and manageability to the hair.

It is a further object of the present invention to provide compositions and methods whereby these proteinaceous materials can be applied to the hair.

DETAILED DESCRIPTION OF THE INVENTION

According to the present invention, it has been found that the antiserum which is formed as a result of injecting a liquid suspension of hair particles into an animal which produces antibodies, is a highly effective proteinaceous conditioning agent for the hair. In particular, it imparts added body to the hair, improves set retention, and renders the hair more manageable.

The antiserum (i.e., antibody-containing serum) is prepared by the following process:

1. injecting an aqueous suspension of hair particles into the body of a live animal which forms antibodies;
2. allowing a sufficient time for antibodies to the hair to form in the blood;
3. withdrawing blood from the animal; and
4. isolating the serum from the blood.

The serum isolated in step (4) contains the hair antibodies and is the antiserum of the present invention.

The hair used in preparing the antiserum can be hair from any mammal but human hair is preferred. The hair should be reduced to a particle size which can be conveniently suspended in an aqueous medium. A particle size less than about 500 microns is satisfactory and a particle size of from about 1 to about 400 microns is preferred.

The hair is suspended by shaking in an aqueous medium prior to injection into the body of the animal. Physiological saline (0.9% NaCl in water) is a particularly suitable medium, although plain water can be used. The aqueous medium can also preferably contain an adjuvant of the type commonly used in the preparation of antibodies, to keep the antigen (hair) in uniform suspension in the injection medium and to localize the antigen in the body tissue into which it is injected. Examples of typical adjuvants are mixtures of vegetable or mineral oils with emulsifiers, e.g., a 90/10 mixture of paraffin oil and sorbitan monolaurate. [See Freund, "Aspects of Active Immunization", *Ann. Rev. Microbiology*, Vol. 1, pp. 291–308 (1947)]. When an adjuvant is used, it is mixed with the water and hair particles to form a water-in-oil emulsion, having hair particles suspended therein.

The concentration of hair particles in the suspension should be from about 0.5% to about 5%. From about 1% to about 3% is preferred. (All percentages herein are by weight unless otherwise specified.)

The injections are typically administered at the rate of from about 25 to about 150 mg. of hair per kg. of animal body weight, and a period of from about 3 to about 21 days is allowed for antibody formation before blood is withdrawn from the animal. A preferred regimen is to administer the hair injections in three equal portions, about 7 days apart and to withdraw the blood about 7 to 20 days after the last injection. Any animal which is capable of forming antibodies in the blood is suitable for use in producing the antiserum of the invention. Typical examples of such animals are rabbits and horses. The injections can be administered into the bloodstream or into the body tissues; however, when an adjuvant is used, it is generally preferred to administer the injection to a tissue, most preferably to muscle tissue.

Isolation of the serum from the blood is accomplished by standard serological techniques. A preferred method is to cause the blood to clot by refrigerating it for a period of about 8 to 15 hours, separating the supernatant serum from the clot, then centrifuging the serum to remove any residual sediment. The serum thus separated is the hair antiserum of the invention. It is believed that skin antiserum can be produced in a manner similar to that described above, by using a ground skin or callous instead of hair, and that such antiserum can be applied to the skin to improve the condition of the skin.

To condition the hair, the hair is contacted with an effective amount of the hair antiserum of the invention (i.e., an amount which is sufficient to achieve a noticeable conditioning effect on the hair). Preferably, the hair antiserum is first diluted in a suitable diluent or carrier, which does not react with the antiserum, and is then applied to the hair. Water is a suitable diluent or carrier. Generally, an amount of antiserum of at least about 0.001 g. per usage on the human head is suitable to achieve a noticeable conditioning effect. Preferably, the antiserum is applied to the hair at the rate of about 0.001 g. to about 1.0 g., and most preferably from about 0.01 g. to about 0.5 g. per usage.

It is also desirable to use a shampoo composition as the carrier, in which case the hair can be conveniently and simultaneously shampooed and treated with the antiserum. The shampoo compositions comprise from about 10% to about 50% of a soap or synthetic detergent (preferably an anionic, cationic or nonionic synthetic detergent), and from about 0.1% to about 20% (preferably from about 2% to about 10% of the antiserum described hereinbefore.

The term "soap" as used herein is meant to designate alkali metal soaps such as the sodium and potassium salts of the higher fatty acids of naturally occurring plant or animal esters, e.g., palm oil, coconut oil, babassu oil, soybean oil, castor oil, tallow, whale and fish oils, grease and lard and mixtures thereof. Sodium and potassium soaps can be made by direct saponification of the fats and oils or by the neutralization of the fatty acids which are prepared in a separate manufacturing process. Examples of suitable soaps are the sodium, potassium, ammonium and alkylol-ammonium salts of higher fatty acids ($C_{10}$–$C_{20}$). Particularly useful are the sodium and potassium salts of the mixtures of fatty acids derived from coconut oil and tallow, i.e., sodium or potassium tallow and coconut soap.

Anionic synthetic detergents which can be used in the shampoo compositions of the present invention can be broadly defined as the water-soluble salts, including the alkali metal, ammonium and substituted ammonium salts, of organic sulfuric reaction products having in their molecular structure an alkyl radical containing from about 8 to about 22 carbon atoms and a radical selected from the group consisting of sulfonic acid and sulfuric acid ester radicals.

Important examples of the synthetic detergents which can be used are the following: alkali metal (e.g., sodium and potassium), ammonium and substituted ammonium (e.g., lower alkyl ammonium) salts of the following: alkyl sulfates, especially those obtained by sulfating the higher alcohols produced by reducing the glycerides of tallow or coconut oil; random paraffin sulfonates, in which the alkyl group contains from about 8 to about 22 carbon atoms, prepared by treating random paraffin hydrocarbons in sulfur dioxide and chlorine in the presence of light followed by treating with a base; branched or linear alkyl benzene sulfonates, in which the alkyl group contains from about 8 to about 18 carbon atoms, preferably from about 10 to about 14 carbon atoms, especially those of the types described in U.S. Pat. Nos. 2,220,099, Guenther et al., Nov. 5, 1940, and 2,477,383, Lewis, July 26, 1949; sodium alkyl glyceryl ether sulfonates, especially those ethers of the higher alcohols derived from tallow and coconut oil; coconut oil fatty acid monoglyceride sulfates and sulfonates; sulfuric acid esters of the reaction product of one mole of a higher fatty alcohol (e.g., tallow or coconut alcohols) and from about 1 to about 6, preferably about 3 moles of ethylene oxide; alkyl phenol ethylene oxide ether sulfates with about 4 units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; fatty acid amides of methyl taurine in which the fatty acids, for example, are derived from coconut oil; sulfonated olefins of U.S. Pat. No. 3,332,880, Kessler et al., July 25, 1967; and others known in the art, a number being specifically set forth in U.S. Pat. Nos. 2,486,921, Byerly, Nov. 1, 1949, 2,486,922, Strain, Nov. 1, 1949, and 2,396,278, Lind, Mar. 12, 1946.

The nonionic synthetic detergents which can be used in the shampoos of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic". These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensaion product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide with ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula,

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyl-di(3-hydroxypropyl)amine oxide, and dimethylhexadecylamine oxide.

5. Long chain tertiary phosphine oxides corresponding to the following general formula,

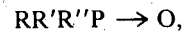

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide, tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide, and
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide, and
3-hydroxy-4-dodecoxybutyl methyl sulfoxide.

The zwitterionic synthetic detergents can also be used in the shampoos of the present invention. These detergents can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

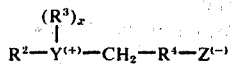

$$R^2 - Y^{(+)} - CH_2 - R^4 - Z^{(-)}$$
with $(R^3)_x$ on Y wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

Amphoteric synthetic detergents are also useful in the compositions of the present invention. These detergents can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, dodecyl-beta-alanine, N-alkyl-taurines such as the one prepared by reacting dodecylamine with sodium isethionate according to the teaching of U.S. Pat. No. 2,658,072, Kosmin, Nov. 3, 1953, N-higher alkyl aspartic acids such as those produced according to the teaching of U.S. Pat. No. 2,438,091, Lynch, Mar. 16, 1948, and the products sold under the trade name "Miranol" and described in U.S. Pat. No. 2,528,378, Mannheimer, Oct. 31, 1950.

Cationic synthetic detergents include those quaternary ammonium, quaternary phosphonium, and ternary sulfonium compounds containing a single straight chain or branched aliphatic radical containing from about 6 to about 20 carbon atoms such as dodecyltrimethylammonium chloride; nonylbenzylethyldimethylammonium nitrate; tetradecylpyridinium bromide; octadecylbutylpropylmethylphosphonium nitrate; decyldimethylsulfonium chloride; etc.

In addition to the ingredients described hereinbefore, the shampoo compositions of the invention can also contain other conventional shampoo ingredients.

It is desirable and preferred to employ pH adjusting agents in shampoo compositions to adjust the pH of the composition to within the range of from about 6 to 8, preferably from about 6.5 to about 7.5. Such agents include buffers such as the sodium, potassium or ammonium citrates, phosphates, borates, carbonates, etc., as well as acids and bases such as NaOH, HCl, etc.

It is also desirable to employ thickening agents such as carrageean, polyethylene glycol distearate, hydroxyethyl cellulose (e.g., an HEC which has a degree of substitution of about 2.5 and a 1% solution of which has a viscosity of 3,000 – 4,000 cp. at 25° C.) and cationic cellulose ethers of the type disclosed in U.S. Pat. No. 3,472,840, Slone et al., issued Oct. 14, 1969, which is incorporated herein by reference.

These shampoos can also contain dyes, preservatives such as benzyl alcohol, ethanol or Bronopol (Goldschmidt Chemical Co.), perfumes, opacifiers such as stearyl alcohol, octyl alcohol or behenic acid, antibacterial agents, antidandruff agents such as sulfur, salicylic acid, resorcinol, zinc pyridinethiol N-oxide, or selenium sulfide, etc. Sequestering agents, such as citric acid or salts of ethylenediaminetetraacetic acid may also be used in these compositions.

Shampoo compositions generally contain from about 40% to about 85% water.

The invention will be further illustrated by the following examples.

EXAMPLE I

Whole virgin, brunette European human hair was ground in a 40 mesh Wiley Mill to a particle size of less than 420 microns (i.e., all of the particles passed through a 40 mesh screen). The hair was suspended by vigorous shaking in physiological saline solution at a concentration of 5 g./100 ml. of solution. This suspension was then mixed with an equal volume of Freunds Complete Adjuvant (Bacto Control 577835 from Difco Laboratories, Detroit, Mich.), and vigorously shaken to form a stable suspension containing 100 mg. of hair per 4 ml.

Five white rabbits (each weighing between 3 and 5 kg.) were each injected intermuscularly with 4 ml. of the suspension (2 ml. per hip) with an 18 gauge needle. The injections were repeated 7 days later and again 14 days later, giving a total of 300 mg. of hair injected per rabbit. Three of the rabbits were bled 16 days after the last injection and one rabbit was bled 8 days after the last injection. The fifth rabbit died. The blood from the four bled rabbits was combined, and placed in a refrigerator overnight and the clot which formed was separated from the serum by decantation. The serum was then spun in a Scovill centrifuge at 400 rpm for 40 minutes to remove any additional sediment. This serum is referred to as the test serum in the remainder of this example.

A batch of control serum was similarly prepared from a group of control rabbits which had not been injected with the hair suspension.

Three brown virgin European hair switches were tested in the following manner:

One switch was dipped in a solution of the test serum, prepared by diluting 1 part serum to 3 parts distilled water. A second switch was dipped in a similar solution made with the control serum, and a third switch was dipped in distilled water. All these switches were rinsed with distilled water and allowed to dry. It was noted that the switches treated with the two serum solutions dried more slowly than the switch treated with water. After drying, the switches were combed. Both serum-treated switches had more body (i.e., were mpore difficult to pull a comb through) than the water-treated switch, and this effect was much more pronounced in the switch treated with the test serum than in the one treated with the control serum.

EXAMPLE II

A shampoo composition is prepared by mixing the following ingredients in the proportions indicated:

| Ingredient | Parts by Weight |
|---|---|
| Sodium coconut fatty alcohol sulfate | 23.0 |
| Sodium stearate | 8.7 |
| Sodium sulfate | 0.8 |
| Trisodium phosphate | 2.1 |
| Perfume | 1.0 |
| Hair antiserum* | 3.0 |
| Water | balance to 100 |

*The test serum of Example I.

This shampoo, when used in the normal manner (i.e., about 10–15 grams per usage), leaves the hair with improved body, manageability, and set retention properties compared to a similar shampoo in which no hair antiserum is present.

What is claimed is:

1. A method of conditioning hair comprising the step of contacting the hair on the head of humans with an effective conditioning amount of an antiserum prepared by the process of:
   A. injecting an aqueous suspension of human hair particles into the body of a live animal which produces antibodies;
   B. allowing a sufficient time for antibodies to form in the blood;
   C. withdrawing blood from the animal; and
   D. isolating the antiserum from the blood.

2. The method of claim 1, wherein the amount of antiserum applied to the hair is from about 0.001 g. to about 1.0 g.

3. The method of claim 2, wherein the amount of antiserum is from about 0.01 g. to about 0.5 g.

4. The method of claim 2, wherein the antiserum is applied to the hair in an aqueous carrier.

5. A shampoo composition comprising in an aqueous carrier from about 10% to about 50% of a soap or synthetic detergent and from about 0.1% to about 20% of an antiserum prepared by a process comprising the steps of:
   A. injecting an aqueous suspension of human hair particles into the body of a live animal which produces antibodies;
   B. allowing a sufficient time for antibodies to form in the blood;
   C. withdrawing blood from the animal; and
   D. isolating the antiserum from the blood.

6. The composition of claim 5, wherein the amount of antiserum in the composition is from about 2% to about 10%.

* * * * *